(12) United States Patent
Mochizuki et al.

(10) Patent No.: US 10,667,739 B2
(45) Date of Patent: Jun. 2, 2020

(54) OLFACTION TEST DEVICE

(71) Applicants: Shimadzu Corporation, Kyoto (JP); Takanori Mochizuki, Kyoto (JP)

(72) Inventors: Takanori Mochizuki, Kyoto (JP); Junichi Kita, Kyoto (JP); Motoo Kinoshita, Kyoto (JP)

(73) Assignees: Shimadzu Corporation, Kyoto (JP); Takanori Mochizuki, Kyoto (JP)

( * ) Notice: Subject to any disclaimer, the term of this patent is extended or adjusted under 35 U.S.C. 154(b) by 279 days.

(21) Appl. No.: 15/656,085

(22) Filed: Jul. 21, 2017

(65) Prior Publication Data

US 2019/0021645 A1    Jan. 24, 2019

(51) Int. Cl.
*A61B 5/00* (2006.01)

(52) U.S. Cl.
CPC .......... *A61B 5/4064* (2013.01); *A61B 5/4011* (2013.01); *A61B 5/4088* (2013.01); *A61B 5/742* (2013.01)

(58) Field of Classification Search
CPC ... A61B 5/4064; A61B 5/4011; A61B 5/4088; A61B 5/742
See application file for complete search history.

(56) References Cited

U.S. PATENT DOCUMENTS

| | | | | |
|---|---|---|---|---|
| 3,795,438 A | * | 3/1974 | Westenholz | A63J 5/00 352/85 |
| 6,325,475 B1 | | 12/2001 | Hayes et al. | |
| 6,357,726 B1 | * | 3/2002 | Watkins | A61L 9/122 261/26 |
| 2015/0112161 A1 | * | 4/2015 | Mills | A61B 5/0875 600/303 |
| 2015/0216414 A1 | * | 8/2015 | Wood | G09B 7/00 600/303 |

FOREIGN PATENT DOCUMENTS

| | | |
|---|---|---|
| JP | 62-231638 A | 10/1987 |
| WO | WO-2013150446 A1 * 10/2013 | ............... A61B 5/00 |
| WO | 2015/061313 A1 | 4/2015 |

OTHER PUBLICATIONS

Japanese Office Action dated Jul. 3, 2018, in connection with corresponding JP Application No. 2015-004622 (8 pgs, including English translation).
Office Action dated Dec. 4, 2018 in corresponding Japanese Application No. 2015-004622; 6 pages including English-language translation.

* cited by examiner

*Primary Examiner* — Eric J Messersmith
(74) *Attorney, Agent, or Firm* — Maier & Maier, PLLC (57) ABSTRACT

An olfactory examination apparatus includes: an odor generating unit having an odorant generating mechanism that stores an odorant and generates an odorous gas having a defined concentration or an defined intensity and an odorless gas generating mechanism; a gas supply unit configured to alternately supply an odorous gas or an odorless gas having a defined concentration or a defined intensity of the odor from the odorant generating mechanism and the odorless gas generating mechanism to an examinee through an odor presentation mechanism placed on a nostril portion of the examinee, and a reply unit that allows the examinee to express an answer when smelling the odorant in order to examine an olfactory function.

7 Claims, 5 Drawing Sheets

| ODOR INDEX | ODOR CONCENTRATION | 1/ODOR CONCENTRATION | FOR 200 ml |
|---|---|---|---|
| 2 | 1.58 | 0.631 | 126.2 |
| 4 | 2.51 | 0.398 | 79.6 |
| 6 | 3.98 | 0.251 | 50.2 |
| 8 | 6.31 | 0.158 | 31.7 |
| 10 | 10.00 | 0.100 | 20.0 |
| 12 | 15.85 | 0.063 | 12.6 |

OLFACTION TEST DEVICE

BACKGROUND OF THE INVENTION

Field of the Invention

The present invention relates to an olfactory examination apparatus used in an olfactory function examination.

Description of the Related Art

Since a standard odor has not been found yet, an olfactory function examination is difficult among five senses, compared to visual, auditory, and tactile examinations, or the like, and there is no suitable and simple examination apparatus at this time.

Incidentally, in recent years, it is known that the olfactory function declines in an early stage of Alzheimer's disease, Parkinson's disease, or the like. The olfactory function examination is attracting attention not only as a diagnosis of normal olfactory disorders such as anosmia and dysgeusia, but also as an early diagnosis of brain diseases such as Alzheimer's disease and Parkinson's disease.

For example, a method of examining early Alzheimer's type dementia based on a difference in feeling of odors of peanut butter has been proposed (see Journal of the Neurological Science, Volume 333, Issue 1, Pages 19-24, 15 Oct. 2013).

In the peanut butter examination of Journal of the Neurological Science, Volume 333, Issue 1, Pages 19-24, 15 Oct. 2013, eighteen patients who have high possibilities of Alzheimer's type dementia, twenty four patients who suffer from light cognitive function disorders, twenty six patients who are diagnosed with dementia other than Alzheimer's type, and twenty six controls who have no cognitive function disorder are selected as examinees. In addition, while the examinee closes her/his eyes, a vertical ruler is placed on a position of nostrils, a sealed container housing one tea spoon (16 g) of the peanut butter is placed in a position of 30 cm under the nostrils, a lid of the sealed container is opened, and what is the odor is asked to the examinee. If the examinee does not recognize the smell, the same process is repeated by lifting the position of the container by 1 cm higher (nostrils). Then, a position where the examinee feels the odor is recorded.

In a group of patients suspected to have Alzheimer's type dementia, an average subnasal position at which the odor is felt by a left nose was 5.1 cm, and an average subnasal position for a right nose was 17.4 cm. Therefore, there was a clear different between the left and right noses, and the olfactory function of the left nose is worse. If these are evaluated for the difference between left and right numerical values (left–right), twenty six controls had an average of 0.0. In comparison, the Alzheimer group had an average of −12.4 cm, the group of patients who suffer from light cognitive function disorders had an average of −1.9 cm, and the group of dementias other than Alzheimer had an average of 4.8 cm. Therefore, there was a clear difference between the Alzheimer's disease group and the other groups.

In this manner, in the early stage of Alzheimer's type dementia, a strong olfactory cortex abnormality occurs in the left hemisphere. Assuming that the left and right numerical values are identical in the early stage of Alzheimer's type dementia, it is possible to determine or suggest a risk of Alzheimer's type dementia by examining the odor difference between the left and right noses.

In particular, for treatment of the Alzheimer's disease, its progression may be delayed in morbidity, but a medicine for perfect treatment has not yet been developed. It can be expected that a patient can be recovered to a state close to normal if the disease is found in the early stage. In addition, it has been proved that the progress of the disease can be suppressed considerably as recognized by an example of Aricept (Registered Trademark). Therefore, it is important to early detect the Alzheimer's disease. If a patient is conscious, the progression of the disease has started. Accordingly, how to detect a change of the brain (olfactory) function preventively from a health diagnosis perspective is an important problem. Furthermore, in the recent studies, it has been reported that, when a symptom of Alzheimer's disease is detected in the early stage, the symptom is improved by brain stimulation caused by exercise or linguistic stimulation or brain stimulation caused by odor. Therefore, the preventive early diagnosis is also important to deal with appropriate symptomatic improvement.

For example, in the peanut butter examination, a method is employed, in which an olfactory function is examined by gradually bringing a peanut butter solid close to a nose far from the nose to adjust the intensity and measuring the distance from the nose using a ruler. In general, as the olfactory function test, different odorants are placed beside the nose, and a recognition examination is performed as to whether it smells or not.

However, although these methods are very simple, the odor intensity is defined on the basis of a distance from the nose, and it is performed manually. In addition, considering a fact that the odorant is vaporized and carried by an air current, it is difficult to provide a reproducible odor intensity. Therefore, a deviation occurs in the examination, and this remarkably degrades reliability of the examination. Furthermore, the olfactory function has a so-called adaptation phenomenon in which, if the same odor smelled for a long time, its olfactory sensitivity is lowered. Moreover, although comparison with the odor smelled just before can be performed accurately, comparison with the odor smelled while ago is not satisfactory. An examination device considering this fact does not exist, and it is difficult to examine the olfactory function with reproducibility.

Although whether or not the odorant is perceived is examined in the method of the related art, it is difficult to perform quantitative evaluation in this case. In addition, it is difficult to comprehensively determine olfactory functions such as an odor intensity, different odorants, a mixed odorant, and the like.

In short, the olfactory function examination of the related art is far from quantitative or comprehensive olfactory function examination, and, at this time, there is no device that can allow suitable and easy examination as a first item of a health diagnosis as in a visual or auditory function test.

SUMMARY OF THE INVENTION

In view of the aforementioned problems of the related art, the invention provides an olfactory examination apparatus capable of suitably and easily performing quantitative or comprehensive olfactory function examination as a first item of a health diagnosis as in a visual or auditory function test.

(1) According to an aspect of the invention, there is provided an olfactory examination apparatus including: an odor generating unit having an odorant generating mechanism that stores an odorant and generates an odorous gas having a defined concentration or an defined intensity and an odorless gas generating mechanism; a gas supply unit configured to alternately supply an odorous gas or an odorless gas from the odorant generating mechanism and the odorless gas generating mechanism to an examinee through an odor presentation mechanism placed on a nostril portion of the examinee; and a reply unit that allows the examinee to express an answer when smelling the odorant, so that the odorous gas and the odorless gas from the gas supply unit are alternately supplied to the examinee.

(2) In the olfactory examination apparatus as in (1), the odorant generating mechanism may adjust the concentration such that the odorant intensity changes in a logarithmic scale. This is because a human nose has sensitivity proportional to a logarithm of the concentration.

In the olfactory examination apparatus as in (1) or (2), the odorant generating mechanism forms an independent flow path to prevent a crosstalk of the odorant and provide a constant concentration even after a time elapses. Specifically, the odorant generating mechanism includes a small-sized reservoir, a diffusion tube, a permeator, an odorant cartridge, or the like. In addition, the odorless gas generating mechanism may be a tube filled with, for example, a high purity clean air (substantially 99.9999%) or activated carbon to the odorless gas. However, similar to the odorant generating mechanism, it is necessary to ensure an odorless property at all times.

In the olfactory examination apparatus described in (1) and (2), the odorant generating mechanism includes a plurality of odorant generating mechanisms that store a single type of the odorant and have an odorant intensity changing stepwise, a plurality of odorant generating mechanisms that store different odorants, or an odorant generating mechanism in which two or more types of odorants are mixed.

Meanwhile, the odorless gas generating mechanism may be provided by dedicatedly using an odorant cartridge that does not store any odorant. However, a hollow pipe-shaped body or passage where at least odorless clean air can pass may be employed.

In a case where the odorous gas and the odorless gas are alternately supplied to nostrils from the odorant generating mechanism and the odorless gas generating mechanism, preferably, the odorous gas or the odorless gas is alternately smelled by the examinee in synchronization with respiration of the examinee. In this case, expiration and inspiration timings may be displayed on a computer screen, and the examinee may be forced to smell the odor at reasonable timings. This is because, since impression of the odorant or the intensity usually disappears immediately, two comparison target odors are smelled within a short time. Furthermore, depending on the odorant, it is not necessary to switch supply of the odorous gas and supply of the odorless gas to nostrils every time. Instead, supply of the odorless gas may be performed continuously two or more times until the next supply of the odorous gas. Such an aspect is also included in a category of the alternate supply.

(3) In the olfactory examination apparatus as in (1) or (2), the odor presentation mechanism may have a unit for selectively supplying the odorous gas or the odorless gas to any one of left and right nostrils or both the left and right nostrils.

As a unit for selectively supplying the odorous gas or the odorless gas, piping that provides the odorous gas to only one of nostrils, or in the case of a mechanism that blocks one of nostrils, a suitable pipe may be employed. Alternatively, a unit for pressing from the outside or plugging nostrils may also be employed. A mechanism for selecting nostrils is selectively controlled such that the odorous gas or the odorless gas is supplied to any one of left and right nostrils or both the left and right nostrils depending on the examination protocol. Note that, in order to supply the odorous gas to the nostrils, it is preferable to insert them directly into the nostrils such that the exhaled breath of the examinee does not mix as much as possible.

(4) In the olfactory examination apparatus as in any one of (1) to (3), the odor generating unit may have a cartridge housing which is intermittently driven, an odorant cartridge and a blank cartridge of an odorless gas may be arranged in the cartridge housing, and the gas supply unit may be arranged in a predetermined position on a movement locus of the cartridge housing.

The cartridge housing is provided with a plurality of insertion holes where a plurality of odorant cartridges and at least one of the blank cartridges of the odorless gas are inserted. The odorant cartridges and the blank cartridges of the odorless gas are intermittently driven to move to a position of the gas supply unit arranged in a predetermined position on its movement locus. Preferably, in order to constantly generate the odorant, a temperature of the cartridge housing (odorant cartridge) is controlled.

(5) In the olfactory examination apparatus as in (4), the odorant cartridge may have check valves provided in both ends of a hollow tubular shape, and particles containing odorants may be packed in a middle portion of the odorant cartridge.

As the particles containing odorants, particles having surfaces where the odor species is adsorbed, such as Tenax (registered trademark), are preferably employed. In the case of such particles, it is possible to easily adjust and change the odor intensity depending on the number of particles packed in the cartridge.

(6) In the olfactory examination apparatus as in any one of (1) to (3), the odor generating unit may increase or decrease a flow rate of the odorous gas from the odorant generating mechanism stepwise in a place where odorless air of a constant amount flows to change a concentration or an intensity of the odorant.

(7) In the olfactory examination apparatus as in any one of (1) to (6), the reply unit may have a voice recognition function, so that the answer can be recognized verbally when an examinee smells the odorant.

The voice recognition function may be implemented using voice recognition software already commercially available in the market.

(8) The olfactory examination apparatus may further include a display unit configured to display a reply content of the reply unit.

As the display unit for displaying the reply content, a panel display such as a liquid crystal display may be employed to display a reply made by the reply unit when the examinee detects the smell of the odorant and a comprehensive evaluation result based on the reply content.

(9) In the olfactory examination apparatus described above, the gas supply unit may have an odor sensor so that it is possible to check whether or not the odorous gas is generated from the odor generating unit.

Any sensor well known in the art may be employed as the odor sensor.

(10) The olfactory examination apparatus described above may further include a unit for checking a reaction of an olfactory brain function of the examinee.

A unit for checking a reaction of the olfactory brain function may include a sensor such as an electroencephalograph or a blood flow meter attached to an examinee.

In the olfactory examination apparatus according to the invention, the odorous gas and the odorless gas are alternately supplied to the examinee from the odor generating mechanism and the odorless gas generating mechanism. Therefore, it is possible to avoid an adaptation phenomenon and easily determine whether or not the supplied gas is odorless because the odorless gas can be checked immediately before. In addition, an answer (reply) is expressed using the reply unit when the examinee smells the odorant. Therefore, using the odorant generating mechanism in which the odorant is prepared, it is possible to provide a reproducible odor intensity. Therefore, a deviation is not generated in the examination, and it is possible to improve reliability of the examination and examine the olfactory function with reproducibility.

Furthermore, it is possible to quantitatively recognize the olfactory intensity sensitivity by changing the concentration of the odorant in a logarithmic scale.

In the olfactory examination apparatus according to the invention, the odorant generating mechanism and the odorless gas generating mechanism are arranged in the cartridge housing which is driven intermittently and are moved to a position of the gas supply unit placed in a predetermined position on a movement locus of the cartridge housing. Therefore, it is possible to compactly assemble the examination apparatus by minimizing the number of complicated movement mechanisms. Even when the temperature of the cartridge housing (odorant cartridge) is controlled to constantly generate the odorant, it is possible to effectively configure the olfactory examination apparatus.

Note that it is possible to rapidly change the concentration or the intensity by increasing or decreasing a flow rate of the odorous gas from the odorant generating mechanism stepwise in a place where odorless air of a constant amount flows.

In the olfactory examination apparatus according to an embodiment of the invention, the odorant cartridge is formed by providing check valves in both ends of a hollow tubular shape and packing particles containing odorants in its middle portion. Therefore, it is possible to easily prepare not only the odor intensities of individual odorant cartridges, but also different odorants, a mixed odorant, and the like. Accordingly, it is possible to comprehensively determine the olfactory function.

In the olfactory examination apparatus according to the invention, the reply unit has a voice recognition function, and an answer can be expressed verbally when the examinee detects the smell of the odorant. Therefore, for example, in a case where the invention is applied to an early diagnosis of Alzheimer's type dementia, typically, most of the examinees of this type of disease are old people. They are unfamiliar with manual operation such as sticks or buttons, fail to operate properly, and may erroneously reply. However, in the olfactory examination apparatus according to the invention, the answer can be expressed (replied) securely through voice. Therefore, even in a case where a risk of Alzheimer's type dementia is determined or indicated, it is possible to appropriately examine the olfactory function.

Furthermore, since the olfactory examination apparatus according to the invention has the display unit for displaying the content of the reply unit, for example, an index for effectively and conveniently recognizing a progression state of Alzheimer's type dementia may also be possible by appropriately devising the display method and the examinee himself/herself can check.

In the olfactory examination apparatus according to the invention, the odor sensor is provided in the gas supply unit, so that generation of the odorous gas can be recognized from the odor generating unit. Therefore, it is possible to prevent in advance an examination mistake caused by not supplying the odorous gas.

The olfactory examination apparatus according to the invention has a unit for checking a reaction of an olfactory brain function of the examinee, so that the reply content made when the examinee smells the odorant can be associated with a change of the brain function. Therefore, it is possible to improve reliability of the reply content and appropriately perform the olfactometric examination.

The olfactory examination apparatus according to the invention can be effectively used, for example, in an early diagnosis of Alzheimer's type dementia or the like or determination of its progression status as described above. However, as an additional effect, the olfactory examination apparatus according to the invention can be used in olfactory stimulation as a preventive measure for healthy persons. In addition, for Alzheimer's type dementia patients, it can be used as a device for strengthening the brain function through odor stimulation.

DETAILED DESCRIPTION OF THE INVENTION

An exemplary olfactory examination apparatus according to an embodiment of the invention will now be described with reference to the accompanying drawings.

Figure 1:
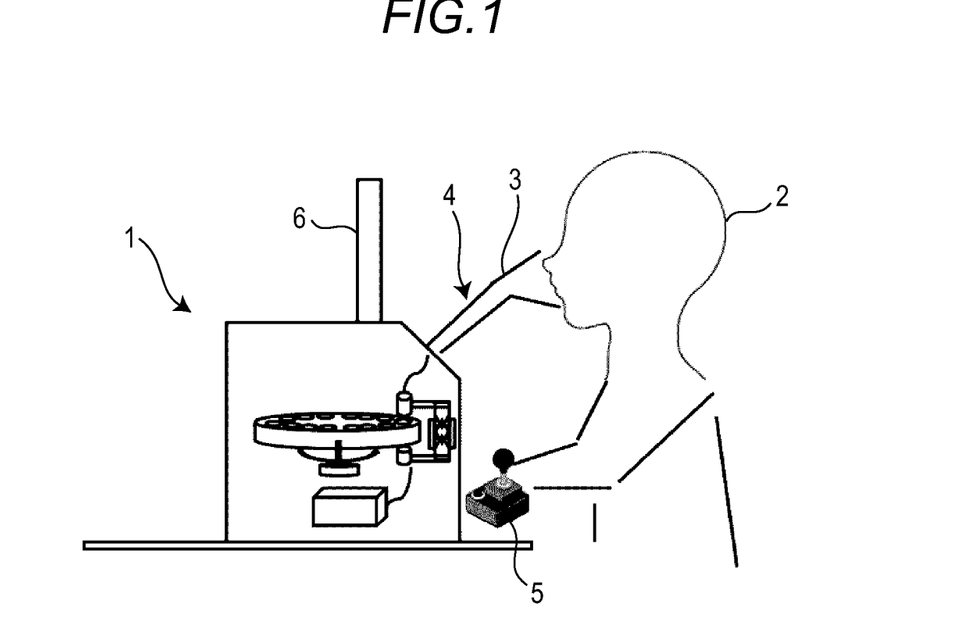
FIG. 1 is a schematic diagram illustrating a whole configuration of an exemplary olfactory examination apparatus according to an embodiment of the invention.

FIG. 1 is a schematic diagram illustrating a whole configuration of an exemplary olfactory examination apparatus according to an embodiment of the invention.

In FIG. 1, an exemplary olfactory examination apparatus according to an embodiment of the invention includes an odor generating unit 1 having an odorant cartridge that houses an odorant described below and a blank cartridge of an odorless gas, a gas supply unit 4 configured to supply the odorous gas or the odorless gas from the odorant cartridge and the blank cartridge of the odorless gas to an examinee 2 through an odor presentation mechanism 3 placed on a nostril portion of the examinee 2, a reply unit 5 used to allow the examinee 2 to express her/his answer when the examinee 2 smells the odorant, and a display unit 6 configured to display contents of the reply unit 5.

Configurations of the odor generating unit 1 and the gas supply unit 4 will be described with reference to FIGS. 2, 3, and 4.

Figure 2:
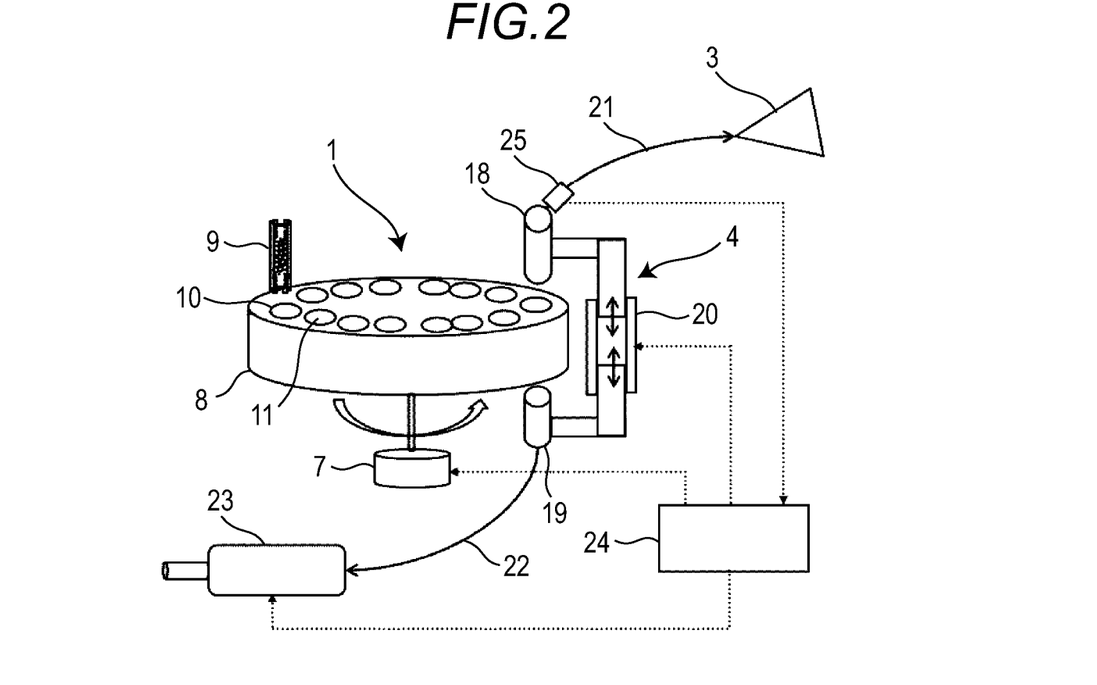
FIG. 2 is a schematic diagram illustrating an exemplary odor generating unit and an exemplary gas supply unit of the olfactory examination apparatus according to an embodiment of the invention.

As illustrated in FIG. 2, the odor generating unit 1 has a cartridge housing 8 intermittently and rotatably driven by a driving mechanism 7, and the cartridge housing 8 has insertion holes 10 and 11 where the odorant cartridges 9 and the blank cartridges of the odorless gas are inserted. Note that, in the example of FIG. 2, the insertion hole 11 corresponds to the blank cartridge of the odorless gas. In addition, the cartridge housing 8 is fixedly supported by a connecting portion (not shown) that connects the cartridge housing 8 and the driving mechanism 7. Furthermore, it is possible to constantly maintain generation of the odorant by controlling a temperature of the cartridge housing 8 using a suitable unit.

When the odorant cartridges 9 and the odorless blank cartridges 11 are placed in the cartridge housing 8, it is not necessary to insert them alternately every other cartridge. Instead, a neutral position may be provided in the cartridge housing 8, and the blank cartridge (insertion hole) 11 of the odorless gas may be inserted into the single place of the neutral position.

Figure 3A:
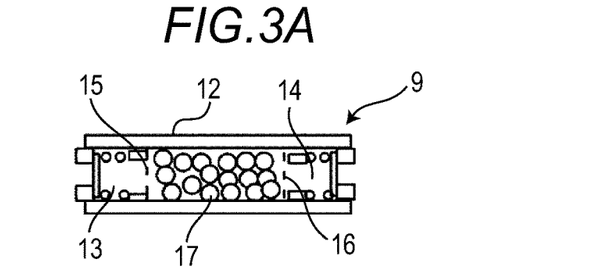
FIGS. 3A to 3C are schematic diagrams illustrating configurations of main parts of an exemplary gas supply unit of the olfactory examination apparatus according to an embodiment of the invention.
Figure 3B:
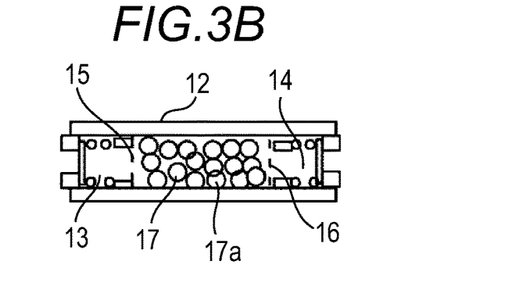
Figure 3C:
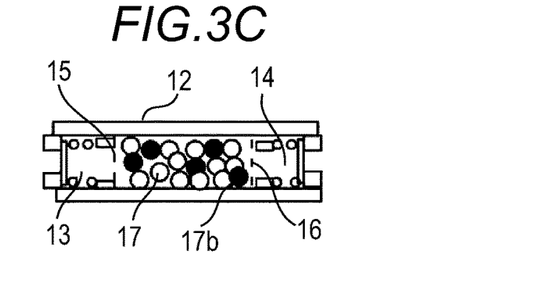
Figure 4:
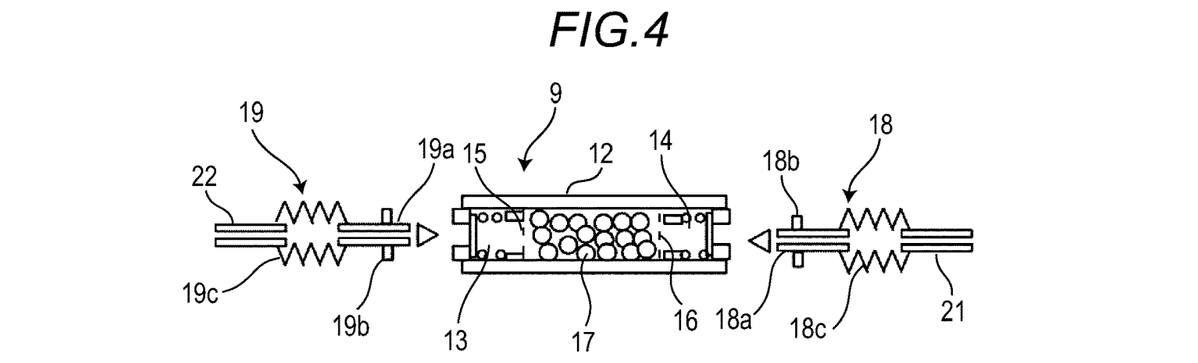
FIG. 4 is a cross-sectional view illustrating an exemplary odorant cartridge of an odor generating unit of the olfactory examination apparatus according to an embodiment of the invention.

FIG. 3 illustrates a specific configuration of the odorant cartridge 9. In FIG. 3, the odorant cartridge 9 is a tubular hollow housing 12 provided with check valves 13 and 14 in both ends, and the check valves 13 and 14 prevent an internal gas inside the hollow from leaking to the outside in a normal state.

Particles 17 containing odorants are packed in the middle part of the tubular hollow housing 12 separated by the check valves 13 and 14 and filters 15 and 16. As the particles 17 containing the odorant, particles having surfaces coated with or adsorbed with an odorant species such as Tenax (registered trademark) are preferably employed. In the case of such particles, odor intensity can be easily adjusted and changed depending on the number of particles 17 containing the odorants packed in the tubular hollow housing 12 for adjusting the amount of the odorant adsorbed with the particles 17.

Note that, as the odorless blank cartridge 11, the insertion hole 11 of the cartridge housing 8 is employed in the example of FIG. 2. Alternatively, an odorant cartridge housing no particles containing the odorant or a simple tubular hollow pipe may also be employed.

FIG. 3A illustrates an odorant cartridge 9 only housing particles 17 containing a single type of odorant. FIG. 3B illustrates an odorant cartridge 9 having different odor intensities obtained by mixing particles 17 containing a single type of odorant and odorless particles 17a coated with or adsorbed with no odor species on the particle surface at a suitable mixing ratio. FIG. 3C illustrates an exemplary mixed odorant cartridge 9 in which particles 17 containing a certain type of odorant and particles 17b containing another type of odorant are mixed at a suitable ratio.

Note that, as the type of odorant, it is difficult to determine which odorant is effective in the olfactometric examination. In the olfactory examination apparatus according to the embodiment of the invention, the type of odorant is not particularly selected. In general, any odorant detectable by a healthy person may be employed. For example, a specific example of the odorant may include India ink, tree, orange, rose, Japanese cypress, garlic, lemon, and the like, which have a difference in the smelling sensitivity between a healthy person and a Alzheimer's patient (refer to Daiki JINBO et al., Specific feature of olfactory dysfunction with Alzheimer's disease inspected by the Odor Stick Identification Test, PSYCHOGERIATRICS, 2011; 11: 196-204).

The gas supply unit 4 that supplies the odorous gas or the odorless gas to the examinee 2 includes a pair of adapters 18 and 19 arranged by interposing the cartridge housing 8 in a predetermined position as illustrated in FIG. 2, an adapter driving mechanism 20 configured to move the adapters 18 and 19 to the odorant cartridge 9 inserted into the cartridge housing 8 and both ends of the blank cartridge 11 of the odorless gas, a channel 21 that connects one of the adapters 18 to the odor presentation mechanism 3, and a channel 22 that connects the other adapter 19 to the clean air supply mechanism 23. Timings of operations of the driving mechanism 7 of the cartridge housing 8, the adapter driving mechanism 20, and the clean air supply mechanism 23 are controlled by the control unit 24. That is, the control unit 24 performs control such that the adapter driving mechanism 20 is driven when the odorant cartridge 9 inserted into the cartridge housing 8 or the blank cartridge 11 of the odorless gas reaches positions of the adapters 18 and 19, and then, the clean air supply mechanism 23 is driven.

Specific configurations of the adapter 18 and 19 will be described with reference to FIG. 4. In FIG. 4, the adapters 18 and 19 have protrusions 18a and 19a, respectively, that presses and opens the check valves 13 and 14 provided in both ends of the odorant cartridge 9 and are provided with sealing portions 18b and 19b, respectively, to prevent the odorous gas from leaking when the check valves 13 and 14 are opened. Note that the elements 18c and 19c are extensible pipes for maintaining degree of freedom of the channels 21 and 22 where the adapters 18 and 19, the odor presentation mechanism 3, and the clean air supply mechanism 23 are connected.

The odorous gas is supplied to the examinee 2 through the odor presentation mechanism 3 as the check valves 13 and 14 are opened by pressing the adapters 18 and 19 to both ends of the odorant cartridge 9, and a clean air supplied from the clean air supply mechanism 23 passes through a middle portion of the odorant cartridge 9 that houses particles containing the odorant. In addition, the odorless gas is supplied to the examinee 2 through the odor presentation mechanism 3 as the clean air from the clean air supply mechanism 23 passes through the odorless blank cartridge 11.

An odor sensor 25 is provided in an appropriate place of the gas supply unit 4 in the middle of the channel 21 that supplies the odorous gas or the odorless gas to the examinee 2 in the example of FIG. 2. As the odor sensor 25, any sensor well known in the art may be employed. For example, when odor molecules are adsorbed with a surface of a metal oxide semiconductor, electric conductivity is improved, and an electric resistance is lowered. Therefore, a sensor that detects generation of the odorant using a change of the resistance is known in the art.

When it is detected that the odorant is not supplied on the basis of the output signal from the odor sensor 25 in accordance with an examination protocol described below, a failure is notified using a suitable alarming unit (not shown). As a result, it is possible to prevent, in advance, an examination mistake generated when the odorous gas is not supplied from the odorant cartridge 9 to the examinee 2.

Figure 5:
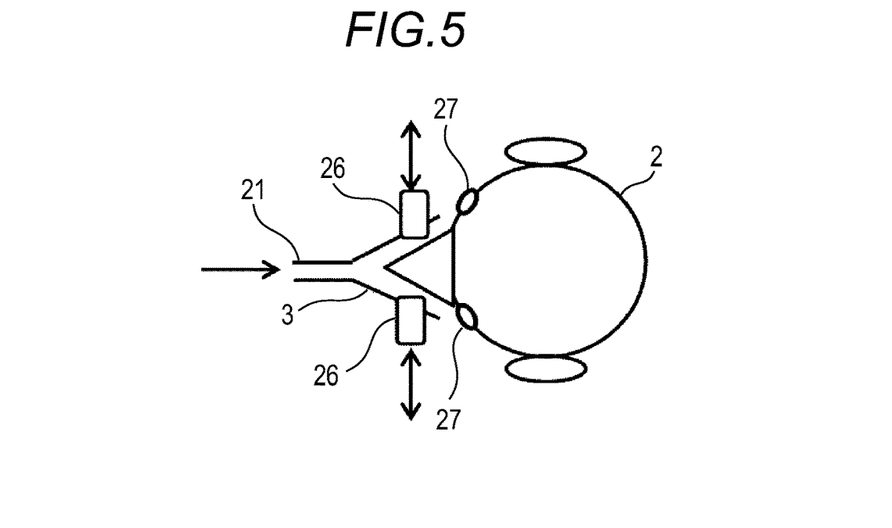
FIG. 5 is a schematic diagram illustrating an exemplary nostril blocking mechanism of the olfactory examination apparatus according to an embodiment of the invention.

FIG. 5 illustrates a configuration of the odor presentation mechanism 3. In FIG. 5, the odor presentation mechanism 3 has a conical shape that surrounds the nostril portion and is held in a head of the examinee 2 using an installation unit such as a band although not shown in the drawings. One end of the channel 21 is connected to the adapter 18, and the other end of the channel 21 is connected to the odor presentation mechanism 3, so that the odorous gas or the odorless gas is supplied to the examinee 2 through the channel 21.

In addition, the odor presentation mechanism 3 is provided with a nostril blocking mechanism 26 that closes one of the left and right nostrils. As the nostril blocking mechanism 26, any suitable mechanism may be employed. For example, a unit that presses and closes the nostrils from the outside is preferable. In addition, more preferably, an independent flow path may be provided in each nostril, so that the odorous gas is supplied to only one of the nostrils, and the odorless gas is supplied to the other nostril.

The nostril blocking mechanism 26 is selectively controlled by the control unit 24 described above in accordance with the examination protocol described below such that the odorous gas or the odorless gas is supplied to any one of the left and right nostrils or both the left and right nostrils.

Note that a unit for checking an olfactory reaction of a brain function of the examinee 2, for example, an electroencephalograph 27 is preferably attached to the examinee 2 to perform the olfactometric examination. As the electroencephalograph 27, a simple type electroencephalograph in which a sensor band is attached to a head has been already on the market. The output signal (brain wave data) from the electroencephalograph 27 is received by the control unit 24 described above, so that the reply content when the examinee 2 smells the odorant can be associated with a change of the brain function. As a result, it is possible to improve reliability of the reply content and perform appropriate examination.

Figure 6:
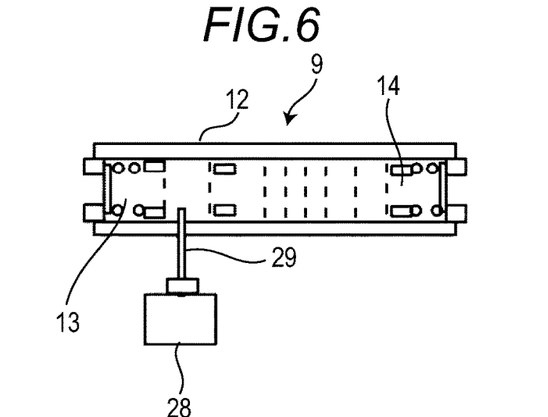
FIG. 6 is a diagram illustrating a modification of the odorant cartridge of the odor generating unit of the olfactory examination apparatus according to an embodiment of the invention.

FIGS. 6 and 7 illustrate modifications of the odorant cartridge 9. In FIG. 6, particles 17 containing odorants are not packed in the odorant cartridge 9 of this example. Using an atomization mechanism 29 protruding from a middle portion of the rear stage of the check valve 13 in the inlet side of the odorant cartridge 9 where the clean air is supplied from the clean air supply mechanism 23 via the channel 22 and the adapter 19 (refer to FIG. 4), an odorant liquid stored in an odorant liquid container 28 is introduced into the odorant cartridge 9 as a sprayed gas, and is supplied to the examinee 2 via the adapter 18 and the channel 21 (refer to FIG. 4) as an odorous gas mixed with the clean air.

Figure 7:
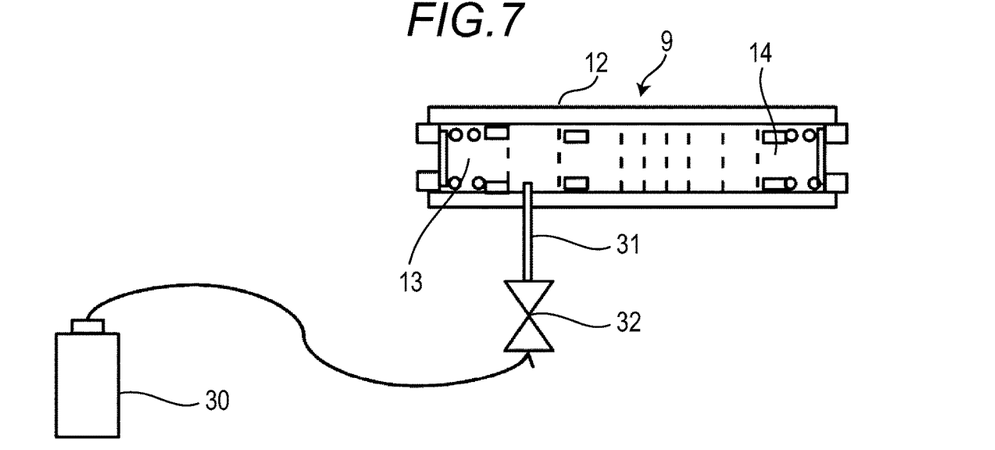
FIG. 7 is a diagram illustrating another modification of the odorant cartridge of the odor generating unit of the olfactory examination apparatus according to an embodiment of the invention.

FIG. 7 illustrates another modification of the odorant cartridge 9. In FIG. 7, similar to the example of FIG. 6, particles 17 containing odorants are not packed in the odorant cartridge 9. Using the atomization mechanism 31 protruding from the middle portion of the rear stage of the check valve 13 in the inlet side of the odorant cartridge 9 where the clean air is supplied from the clean air supply mechanism 23 via the channel 22 and the adapter 19 (refer to FIG. 4), the odorous gas enclosed in the odorous gas reservoir 30 is introduced into the odorant cartridge 9 as a sprayed gas, and is supplied to the examinee 2 via the adapter 18 and the channel 21 (refer to FIG. 4) as an odorous gas mixed with the clean air. Note that the element 32 is a spray control valve.

In the examples of FIGS. 6 and 7, when the olfactometric examination is performed using a plurality of types of odorant liquids or odorous gases, the invention may be easily implemented by sequentially switching flow paths that connect a plurality of odorant liquid containers that stores a plurality of types of odorant liquids or a plurality of odorous gas reservoirs in which a plurality of types of odorous gases are enclosed using a multiple flow path switching mechanism although not shown in the drawings.

Figure 8:
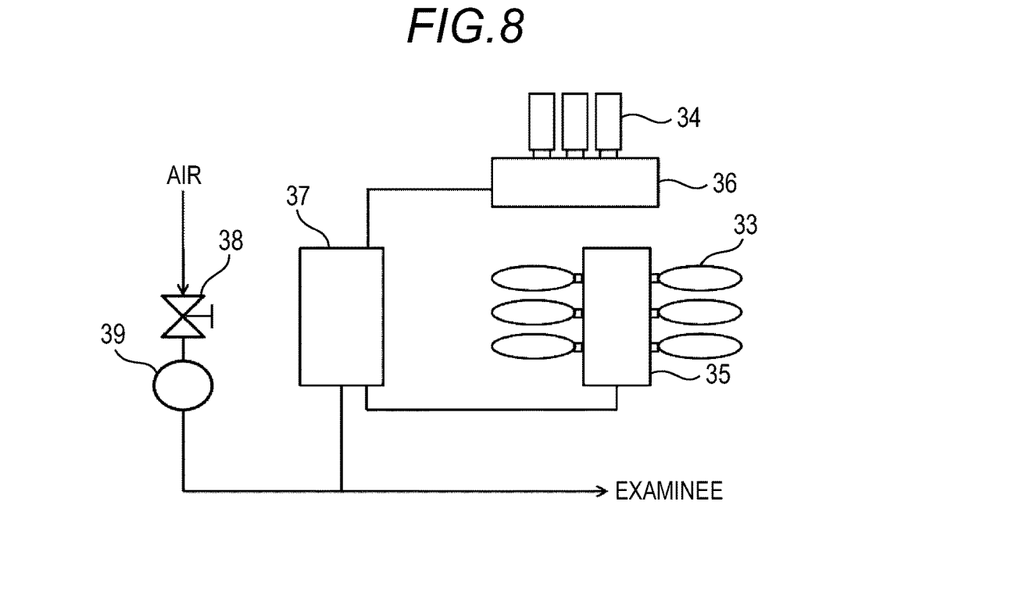
FIG. 8 is a diagram illustrating an olfactory examination apparatus according to another embodiment of the invention.

For example, in order to obtain an olfactory sensitivity for each odorant, an exemplary apparatus of FIG. 8 in which the odorant is arranged in multiple stages, and the odorless gas is interposed to continually change a concentration is proposed. In this apparatus, the odorant stored in the odorant bag 33 or the odorant reservoir 34 is suctioned to a syringe (not shown) of a dilution and mixing device 37 through a flow path switching mechanism 35 and 36 while the odorless gas flows at a constant flow rate (for example, 200 ml/min). Then, the odorous gas discharged from the syringe by intermittently driving (lowering) a plunger of the syringe is mixed with the flowing odorless gas. In this case, a dilution rate is changed by adjusting a lowering speed of the plunger of the syringe because the flow rate of the odorless gas side is constant.

Figure 9:
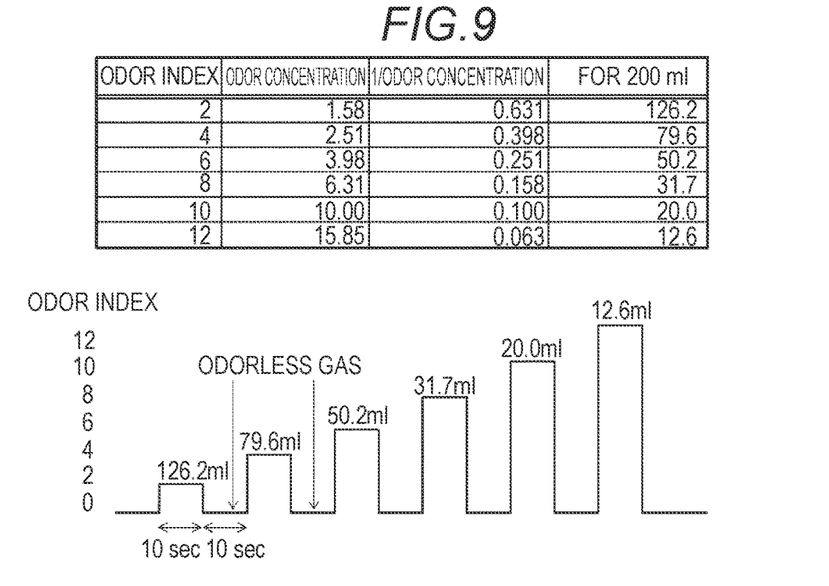
FIG. 9 is a diagram illustrating an exemplary case of changing an odor concentration of the olfactory examination apparatus of FIG. 8 according to an embodiment of the invention.

As illustrated in FIG. 9, if the flow rate of the odorous gas is reduced with respect to the constant flow rate of the odorless gas (for example, 200 ml/min), the dilution rate gradually decreases, and the concentration (intensity) increases (becomes strong) in a logarithmic scale. In comparison, if the flow rate of the odorous gas with respect to the constant flow rate (for example, 200 ml/min) of the odorless gas increases, the concentration decreases in a logarithmic scale. Note that the element 38 is a stop valve, and the element 39 is a flow meter.

Figure 10A:
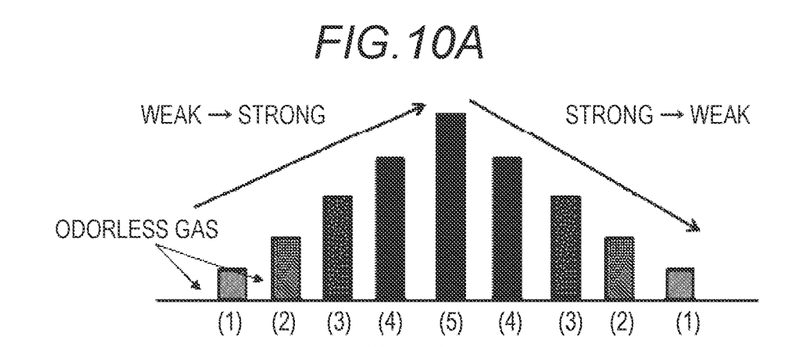
FIGS. 10A to 10C are diagrams illustrating an exemplary examination protocol of the olfactory examination apparatus according to an embodiment of the invention.
Figure 10B:
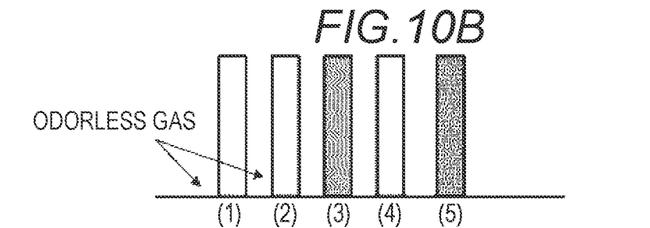
Figure 10C:
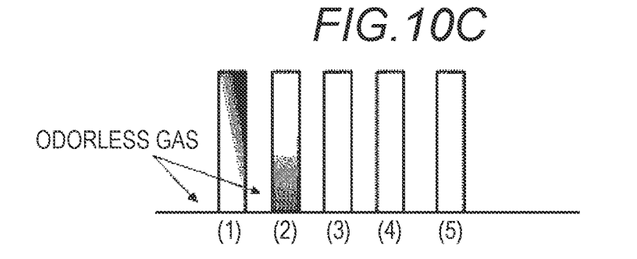

FIGS. 10A to 10C illustrate an exemplary examination protocol. FIG. 10A illustrates an example in which a reaction to the odorant intensity is examined by changing the odorant intensity stepwise from weak to strong (an increasing method in which the odor gradually becomes stronger) or from strong to weak (a decreasing method in which the odor gradually becomes weaker). For example, in the illustrated example, as an example of the step change of the odorant intensity, (1) an odor index of 12, (2) an odor index of 10, (3) an odor index of 8, (4) an odor index of 6, (5) an odor index of 4, (4) an odor index of 6, (3) an odor index of 8, (2) an odor index of 10, and (1) an odor index of 12 are set. In this case, the odorless gas is supplied whenever the odor intensity changes, so that this can be recognized. Therefore, it is possible to more facilitate detection.

Here, in order to provide a scientific meaning, an expression of the odor index is used as an index for the odorant intensity. The odor index is defined by "obtaining a multiple of the dilution (odor concentration) in a case where a gas or water is diluted until it becomes impossible to perceive odor of a sample gas or water by a human olfactory sense using a method prescribed by the Minister of the Environment, and multiplying a logarithm of the odor concentration value by ten" (Article 1 of the Odor Control Law Enforcement Regulation).

That is, the lowest concentration at which the olfaction can detect the odor is a threshold concentration. Assuming that a concentration at which the odor actually exists is set to x (ppm), and the threshold concentration is set to y (ppm), a relationship "x/y=odor concentration" is established, and the odor index becomes "odor index=10×log (odor concentration)" from the odor concentration. In the case of a normal olfactory sense, it becomes odorless initially after diluting the odor by an odor index multiple. However, when the olfactory sensitivity decreases, it becomes difficult to smell even the odor having an odor index of 4 or 6.

Therefore, as the odor index decreases, the odorant intensity becomes weak. Typically, the threshold concentration is set to an odor index of approximately 3 although there is a slight deviation in the sensitivity between healthy persons.

In this case, only the increasing method or the decreasing method may be employed. In addition, it is also effective to perform examination for a plurality of odorants or a plurality of mixed odorants. In addition, in a case where the odorant intensity is changed stepwise, the olfactory sensitivity is sensed as a logarithm of the concentration. Therefore, it is preferable that the concentration be changed in a logarithmic scale. Note that, in a case where the increasing method or the decreasing method is employed, it is possible to more improve examination reliability if it is determined that the examination is effective when the result is within a predetermined range.

FIG. 10B illustrates an exemplary examination for reactions to different odorants. The odorant may include, specifically, India ink, tree, orange, rose, Japanese cypress, garlic, lemon, and the like as described above. In the example of FIG. 10B, the number of odorants (odorant cartridges 9) is set to five (five types).

FIG. 10C illustrates an exemplary examination for reactions to a mixed odorant. That is, FIG. 10C shows a so-called smelling examination. Similarly, in this case, the illustrated example shows five mixed odorant cartridges 9 (refer to FIG. 3C).

In any protocol (a), (b), and (c), the odorless gas (blank) is supplied every time. However, the odorless gas may be supplied twice consecutively depending on the odorant. In this case, it is possible to improve accuracy of the olfactometric examination by excluding the previous odorant influence on the examinee 2. In the examination, differences in reactions are examined on the right nostril, the left nostril, and both the nostrils. However, the protocols (a) to (c) may be performed randomly. A series of these operations are performed using the control unit 24 described above.

FIG. 12 illustrates an exemplary reply screen and an exemplary display unit corresponding to the examination protocols (a), (b), and (c) of FIG. 10. In the example of FIG. 9, a reply is made as simple as possible. Meanwhile, in order to prevent an erroneous reply, the reply is performed while a user sees the reply screen of the display unit 6 such as a liquid crystal display.

Figure 12A:
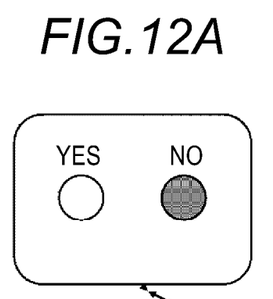
FIG. 12A to 12D is a diagram illustrating an exemplary reply screen and an exemplary display unit corresponding to an examination protocol of the olfactory examination apparatus according to an embodiment of the invention.

The screen (a) is a reply screen corresponding to the protocol for examining a reaction to the odorant intensity (FIG. 10A). An answer "YES" or "NO" is selected and is replied by tilting the stick 5a of the reply unit 5 to the left or the right.

Figure 12B:
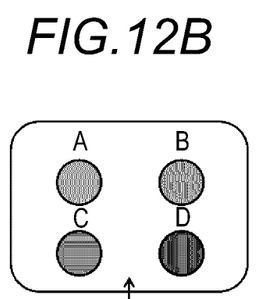

The screen (b) is a reply screen corresponding to the protocol for examining reactions to different odorants (FIG. 10B). A name of the perceived odorant is selected from a selection screen and is replied by tilting the stick 5a of the reply unit 5 upward, downward, leftward, and rightward.

Figure 12C:
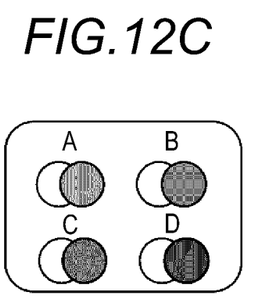
Figure 12D:
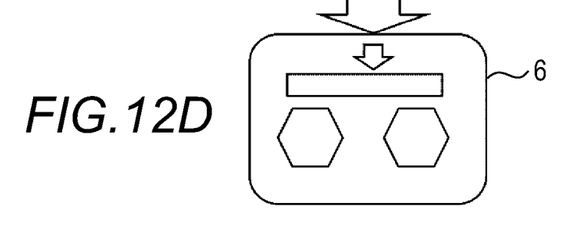

The screen (c) is a reply screen corresponding to the protocol for examining a reaction to a mixed odorant (FIG. 10C). A name of the perceived mixed odorant is selected from different combinations of odorants displayed on the display unit 6 and is replied by tilting the stick 5a of the reply unit 5 upward, downward, leftward, and rightward.

Note that the reply may be performed verbally by looking at the reply screen instead of operation of the stick 5a. Although not shown in the drawings, devices having various types of speech recognition functions are already known, and any one of them may be employed as the reply unit 5.

The screen (d) of FIG. 12 is an exemplary display format of the examination result of the display unit 6. An odorant intensity examination result (corresponding to the examination protocol of FIG. 10A), an odorant examination result (corresponding to the examination protocol of FIG. 10B), a mixed odorant (separation) examination result (corresponding to the examination protocol of FIG. 10C), and an olfactory comprehensive determination result are displayed in each format.

Next, operations of an olfactory examination apparatus according to an embodiment of the invention will be described with reference to the accompanying drawings.

In accordance with the examination protocol (refer to FIGS. 10A to 10C), the odorant cartridges 9 and the blank cartridges 11 of the odorless gas are inserted into the cartridge housing 8 (insertion holes 10 and 11) of the odor generating unit 1. The examinee 2 holds a conical odor presentation mechanism 3 that surrounds the nostril portion on a head using a unit such as a band. In this state, preparation of the olfactometric examination is completed.

First, the air is supplied from the clean air supply mechanism 23 to the blank cartridge 11 of the odorless gas placed in a predetermined position of the cartridge housing 8, and the odorless gas is supplied to the examinee 2 through the odor presentation mechanism 3, so that the examinee 2 checks the odorless state. Then, when the cartridge housing 8 of the odor generating unit 1 is intermittently and rotatably driven by the driving mechanism 7 in accordance with the examination protocol, and the cartridge housing 8 reaches a predetermined position, the adapters 18 and 19 of the gas supply unit 4 are activated by the signal from the control unit 24 and are pressed and bonded to both ends of the odorant cartridge 9. The air is supplied from the clean air supply mechanism 23 and makes contact with and are mixed with the particles 17 containing odorants inside the odorant cartridge 9, so that the odorous gas is supplied to the examinee 2 from the odor presentation mechanism 3.

Figure 11:
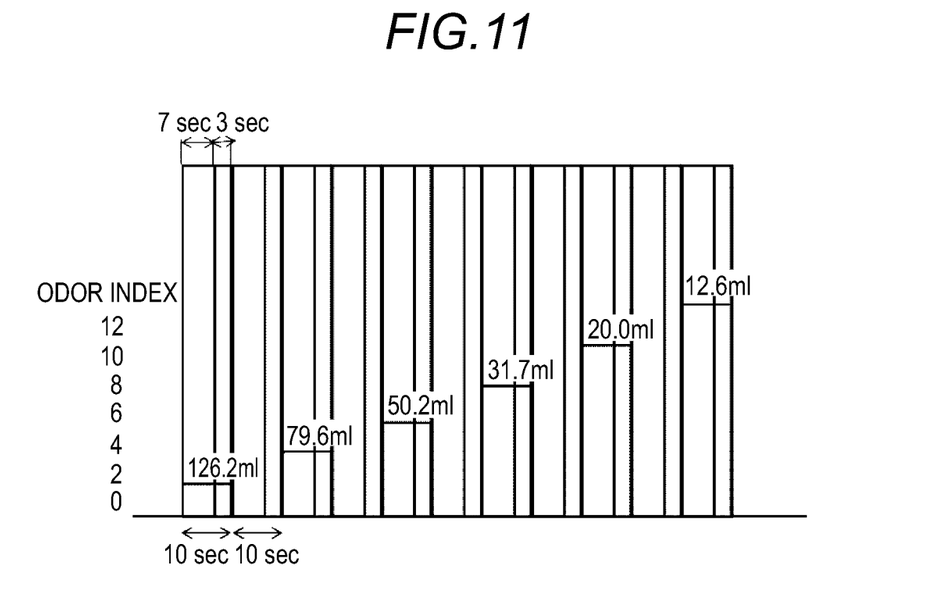
FIG. 11 is a diagram illustrating exemplary expiration and inspiration timings of the olfactory examination apparatus of FIG. 8 according to an embodiment of the invention.

Although the odorous gas and the odorless gas are supplied alternately, in this case, the expiration timing and the inspiration timing are displayed on a screen of a personal computer, so that the examinee may be forced to smell the odor at a suitable timing. FIG. 11 illustrates exemplary expiration and inspiration timings. In the example of FIG. 11, the odorless gas and the odorous gas are supplied at an interval of 10 seconds. However, initial seven seconds of each interval are allocated to expiration, and the next three seconds are allocated to inspiration. This is aimed to exclude the influence of the previous gas as much as possible.

In the examination for the odorants having different intensities, the odorant is supplied to the examinee 2 in accordance with the examination protocol of FIG. 10A, and the replay screen corresponding to the examination protocol of FIG. 10A (refer to the screen (a) of FIG. 12) is displayed on the display unit 6. Then, the examinee 2 selects "YES" or "NO" using the stick 5a of the reply unit 5 and replies it.

For example, "rose" is selected as the odorant, and the odorant cartridges 9 having (1) an odor index of 4, (2) an odor index of 6, (3) an odor index of 8, (4) an odor index of 10, and (5) an odor index of 12 are prepared. In addition, the examinee 2 replies "YES" or "NO" by operating the stick 5a while smelling the odor in accordance with the examination protocol of FIG. 10A. If the examinee 2 does not detect the odorant at all, zero point is given. If the examinee 2 detects the odorant having (1) an odor index of 4, five points are given. These points are displayed on the screen of the display unit 6 using numerical values, graphs, and the like.

Similarly, different odorous gases are supplied to the examinee 2 from the odor generating unit 1 in accordance with the examination protocol of FIG. 10B, and the reply screen (refer to the screen (b) of FIG. 12) corresponding to the examination protocol of FIG. 10B is displayed on the display unit 6. In addition, a name of the perceived odorant is selected from the selection screen using the stick 5a of the reply unit, and is replied.

For example, odorant cartridges 9 that houses (1) rose, (2) Japanese cypress, (3) garlic, (4) Indian ink, and (5) lemon having an odor index of approximately 6 as the odorants are prepared. The examinee 2 selects an answer from the options on the reply screen (refer to the screen (b) of FIG. 12) by operating the stick 5a while smelling the odor in accordance with the examination protocol of FIG. 10B. If the selection is correct, one point is given. If the selection is erroneous, or the examinee 2 fails to detect, zero point is given. If all of them are successful, five points are given. These points are displayed on the screen of the display unit 6 using numerical values, graphs, and the like.

In the examination protocol of FIG. 10C, different combinations of odorants are displayed on the display screen of the reply, and a reply is selected from them. For example, odorant cartridges 9 housing the odorants such as (1) lemon, (2) rose, (3) Japanese cypress, (4) garlic, and (5) Indian ink having an odor index of 6 are prepared, for example, by mixing each odorant with (1) lemon as a base odorant. The examinee 2 selects an answer from the options on the reply screen (refer to the screen (c) of FIG. 12) by operating the stick 5a while smelling the odor in accordance with examination protocol of FIG. 10C. If the selection is correct, one point is given. If the selection is erroneous, or the examinee 2 fails to detect, zero point is given. If all of them are successful, five points are given. These points are displayed on the screen of the display unit 6 using numerical values, graphs, and the like.

Examination is performed by sequentially executing a series of these processes for both of nostrils, the right nostril, and the left nostril in this order using the nostril blocking mechanism 26. After three examination protocols (refer to FIGS. 10A, 10B, and 10C) are performed, olfactory function states are displayed on the display unit 6.

The olfactory examination apparatus according to the invention is not used to determine development of mild cognitive impairment (MCI), but shows its possibility using an olfactory function examination. Therefore, for a healthy person, any examination value is basically 100% correct. If the score is low in any test based on the examination protocol, this indicates a risk of the MCI development.

For example, in the examination protocol of FIG. 10A, typically, the threshold concentration is set to an odor index of approximately 3 although there is a slight deviation in the sensitivity even between healthy persons. If the examinee 2 fails to detect the odor having an odor index of 4 (score five points), it indicates the examinee 2 is cautious. If the examinee 2 fails to detect the odor having an odor index of 6 (score four points), it indicates the examinee 2 is quite suspicious. If the examinee 2 fails to detect the odor having an odor index of 8 or higher (score three points or lower), it indicates the examinee 2 is abnormal and has a risk of MCI development.

The olfactory examination apparatus according to the invention can be employed not only for the purpose of the olfactometric examination, but also for olfactory stimulation as a preventive measure for a healthy person in the olfactometric examination. In addition, the olfactory examination apparatus can be effectively used as a device for strengthening brain functions using odor stimulation for Alzheimer's type dementia patients.

What is claimed is:

1. An olfactory examination apparatus comprising:
   an odor generating unit having an odorant generating mechanism that generates an odorous gas having a defined concentration or a defined intensity by controlling the ratio between the flow rate of odorless gas from a latter described odorless gas generating mechanism and the flow rate of the odor gas supplied from the odor housing unit that stores the odor of a predetermined concentration or intensity and an odorless gas generating mechanism;
   a gas supply unit configured to alternately supply the odorous gas or an odorless gas from the odorant generating mechanism and the odorless gas generating mechanism to an examinee through an odor presentation mechanism placed on a nostril portion of the examinee; and
   a reply unit configured to allow the examinee to express an answer when smelling the odorant, wherein the odor housing unit in the odorant generating mechanism is an odorant cylinder, and the odorant generating mechanism can adjust the defined concentration or the defined intensity such that an odorant intensity changes in a logarithmic scale by aspirating the odorant contained in the odorant cylinder into a syringe and adjusting a lowering speed of the syringe.

2. The olfactory examination apparatus according to claim 1, wherein the gas supply unit is further configured to supply the odorous gas or the odorless gas to any one of left and right nostrils or both the left and right nostrils.

3. The olfactory examination apparatus according to claim 1, wherein the odor generating unit increases or decreases a flow rate of the odorous gas from the odorant generating mechanism stepwise in a place where odorless air of a constant amount flows to change a concentration or an intensity of the odorant.

4. The olfactory examination apparatus according to claim 1, wherein the reply unit has a voice recognition function, so that an answer can be recognized verbally when the examinee smells the odorant.

5. The olfactory examination apparatus according to claim 1, further comprising a display unit configured to display an answer of the reply unit.

6. The olfactory examination apparatus according to claim 1, wherein the gas supply unit has an odor sensor configured to check whether or not the odorous gas is generated from the odor generating unit.

7. The olfactory examination apparatus according to claim 1, further comprising a sensor configured for checking a reaction of an olfactory brain function of the examinee.

\* \* \* \* \*